(12) United States Patent
Apblett

(10) Patent No.: US 9,199,863 B2
(45) Date of Patent: Dec. 1, 2015

(54) IRON COORDINATION POLYMERS FOR ADSORPTION OF ARSENATE AND PHOSPHATE

(75) Inventor: Allen Wallace Apblett, Stillwater, OK (US)

(73) Assignee: The Board Of Regents For Oklahoma State University, Stillwater, OK (US)

( * ) Notice: Subject to any disclaimer, the term of this patent is extended or adjusted under 35 U.S.C. 154(b) by 232 days.

(21) Appl. No.: 13/977,445

(22) PCT Filed: Jan. 3, 2012

(86) PCT No.: PCT/US2012/020086
§ 371 (c)(1),
(2), (4) Date: Jun. 28, 2013

(87) PCT Pub. No.: WO2012/094323
PCT Pub. Date: Jul. 12, 2012

(65) Prior Publication Data
US 2013/0292338 A1 Nov. 7, 2013

Related U.S. Application Data

(60) Provisional application No. 61/429,341, filed on Jan. 3, 2011.

(51) Int. Cl.
*C02F 1/28* (2006.01)
*B01J 20/22* (2006.01)
*B01J 20/30* (2006.01)
*C07C 51/41* (2006.01)
*C02F 101/10* (2006.01)

(52) U.S. Cl.
CPC ............... *C02F 1/285* (2013.01); *B01J 20/226* (2013.01); *B01J 20/30* (2013.01); *B01J 20/3085* (2013.01); *C02F 1/281* (2013.01); *C07C 51/418* (2013.01); *C02F 2101/103* (2013.01); *C02F 2101/105* (2013.01)

(58) Field of Classification Search
CPC ............... C02F 1/285; C02F 2101/103; C02F 2101/105; B01J 20/226; B01J 20/30; B01J 20/3085; C07C 51/418
See application file for complete search history.

(56) References Cited

U.S. PATENT DOCUMENTS

| 4,080,290 A * | 3/1978 | Klantschi et al. ............. 210/683 |
| 2006/0102562 A1 | 5/2006 | Cannon et al. |

FOREIGN PATENT DOCUMENTS

| EP | 061175 A1 | 9/1982 |
| RU | 2161963 C2 | 1/2001 |
| WO | 2004074444 A2 | 9/2004 |

OTHER PUBLICATIONS

Ayyub et al, Size-Induced structural phase transitions and hyperfine properties of microcrystalline Fe2O3, Jan. 1988, Journal of Phystical Chemistry: Solid State Physics, vol. 21, pp. 2229-2245.*

(Continued)

*Primary Examiner* — Matthew O Savage
(74) *Attorney, Agent, or Firm* — Fellers, Snider, Blankenship, Bailey & Tippens, P.C.; Terry L. Watt

(57) ABSTRACT

A method includes combining an aqueous solution of sodium fumarate with an aqueous solution of iron chloride to form a mixture, and obtaining an iron coordination polymer as an amorphous compound formed as a precipitate from the mixture. The iron coordination polymer may be used to bind contaminants, such as arsenate and phosphate from water.

15 Claims, 8 Drawing Sheets

(56) References Cited

OTHER PUBLICATIONS

Murad et al, The Influence of Aluminum Substitution and Crystallinity on the Mossbauer Spectra of Geothite, Jan. 1983, Clay Minerals, vol. 18, pp. 301-312.*

Bassi, Randhawa, and Jamwal, "Mossbauer Study of the Thermal Decomposition of Iron(III) Benzoate and Iron (III) Fumrate", Apr. 25, 1983, pp. 367-374, vol. 69, No. 1983, Publisher: Thermochimica Acta, Published in: Netherlands.

Dziobkowski, Chester J., "Magnetic Properties and Mossbauer Spectra of Several Iron(III)—Dicarboxylic Acid Complexes", 1981, pp. 671-678, Publisher: American Chemical Society, Published in: US.

Kang et al., "Canine Parvoviru Isolate Pome VP2 Gene, Complete CDS", May 8, 2007, Published in: KR.

PCT/US2012/020086—International Search Report published Jun. 2012.

PCT/US2012/020086—International Preliminary Report on Patentability published Jul. 2013.

Dodbiba, Gjergj, et al., "Removal of Arsenic From Wastewater Using Iron Compound: Comparing Two Different Types of Adsorbents in the Context of LCA", Jun. 4, 2009, pp. 688-697, vol. 53, No. 209, Published in: JP.

Chinese State Intellectual Property Office of Peoples Republic of China Search Report, Aug. 25, 2014, Published in Japan.

* cited by examiner

Max. Uptake: 150 mg/g $t_{1/2} \approx 1.1$ hours

IRON COORDINATION POLYMERS FOR ADSORPTION OF ARSENATE AND PHOSPHATE

CROSS REFERENCE TO RELATED APPLICATIONS

This application claims the priority of U.S. Provisional Patent Application No. 61/429,341 entitled "IRON COORDINATION POLYMERS FOR ADSORPTION OF ARSENATE AND PHOSPHATE," filed Jan. 3, 2011, the contents of which are hereby incorporated by reference.

FIELD OF INVENTION

This disclosure is related to coordination polymers in general and, more particularly, iron coordination polymers used for adsorption of arsenate and phosphate.

BACKGROUND OF INVENTION

Arsenic's toxicity to man and other living organisms has led to serious environmental problems and difficulties in procuring suitable drinking water in many parts of the world. In well-oxidized waters, arsenic is present predominately as arsenate ($H_2AsO_4^{-1}$ and $HAsO_4^{-2}$) while under reducing conditions it is usually present as arsenite ($H_3AsO_3$ and $H_2AsO_3^{-1}$) [1]. Since the reduction and oxidation reactions of arsenic are particularly slow, both of these oxidation states can coexist irrespective of the redox conditions [2]. The arsenic (III) species are 25-60 times more toxic than arsenate and are more mobile in the environment [3]. Absorption on mineral surfaces is an important factor that controls the mobility and bioavailability of arsenic. Arsenate adsorption on clays and aluminum and iron oxides is greatest at low pH and decreases with increasing pH while arsenite has a maximum in adsorption to these materials at approximately pH 8.5 [4].

A large variety of materials have been tested for removal of arsenic from water including adsorbents such as phyllosilicates, silica, and hydrous oxides of iron and alumina [3]. The most successful and heavily investigated materials have been iron oxides, especially ferrihydrite [5-12].

SUMMARY OF INVENTION

The invention of the present disclosure, in one aspect thereof, comprises a method that includes combining an aqueous solution of sodium fumarate with an aqueous solution of iron chloride to form a mixture, and obtaining an iron coordination polymer as a precipitate from the mixture. The polymer may be obtained as an amorphous compound and may have the approximate formula of $Fe(O_2CCH{=}CHCO_2)OH \cdot 1.5H_2O$.

The method may include vacuum filtering the amorphous compound from the mixture, and washing the amorphous compound with de-ionized water. The method may also include vacuum drying the amorphous compound.

In one embodiment, the amorphous compound is exposed to water to bind contaminants. The contaminant may be a form of arsenic, or may be a form of phosphorus.

DETAILED DESCRIPTION OF THE PREFERRED EMBODIMENTS

Iron-containing coordination polymers were developed to address the removal of arsenic from water. In recognition that the most important component of many of the reagents for arsenate absorption are iron ions, and that most of these materials are restricted to only binding iron on their surfaces, it was decided that a better approach would be to use an insoluble iron-containing coordination polymer that was capable of using all of its iron content to bind arsenate. In the present disclosure, the term insoluble refers to the property that a substance does not separate or dissolve on a molecular level in water. In this way, an insoluble substance remains intact in an aqueous environment, and able to adsorb the target contaminant.

Several different reagents were prepared by precipitation reactions between aqueous salts iron and either organic dicarboxylates or carboxylate-containing polymers. Examples include precipitates formed by reaction of solutions of sodium polyacrylate, sodium carboxymethylcellulose, ammonium terephthalate, or sodium maleate with an aqueous solution of a ferric salt. Many of these precipitates can adsorb arsenate but the most effective sorbent was prepared by reaction of sodium fumarate with aqueous ferric chloride.

Figure 1:
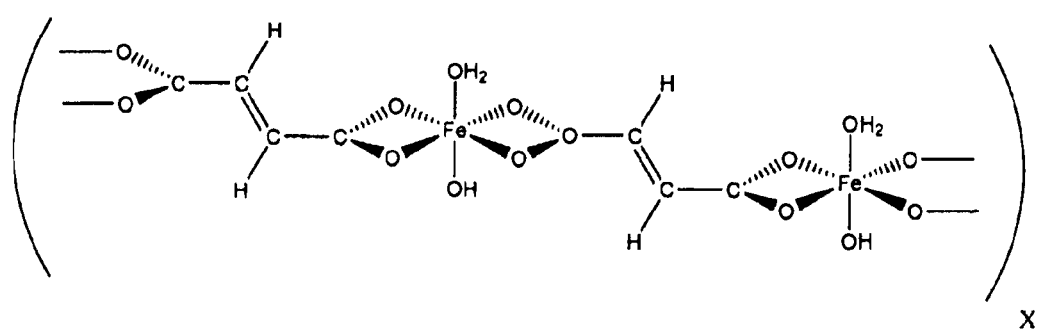
FIG. 1 is an illustration of a possible structure of an iron fumarate coordination polymer of the present disclosure.
Figure 2:
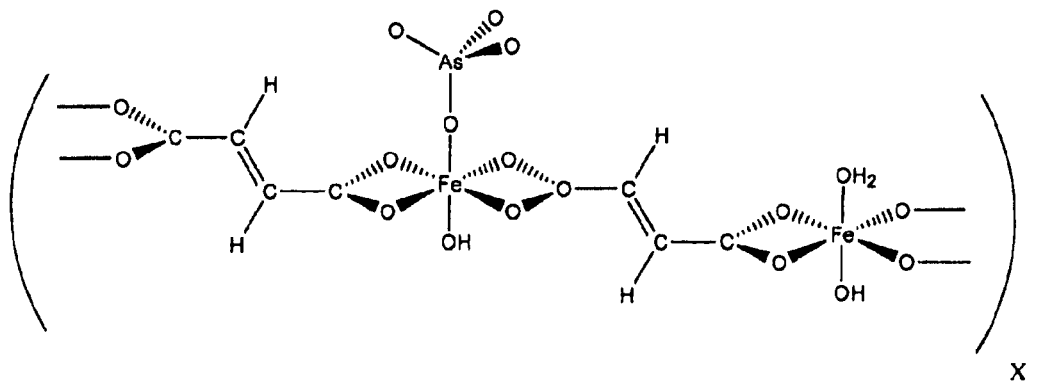
FIG. 2 is an illustration of a possible mode of binding of arsenate to an iron fumarate coordination polymer of the present disclosure.

In one embodiment, the arsenate adsorbing precipitate has the formula of $Fe(O_2CCH{=}CHCO_2)OH \cdot 1.5H_2O$ and an approximation of its structure is shown in FIG. 1. This material can adsorb up to 150 mg arsenate per gram of iron fumarate. The possible binding of arsenate to an iron center by the displacement with water is shown in FIG. 2.

EXAMPLE 1

In one example, iron fumarate (Product 1) was prepared by adding 300 mL of de-ionized water to 30.02 mmol of fumaric acid and 57.98 mmol of sodium hydroxide. Another aqueous solution was prepared using 300 mL of de-ionized water and 14.93 mmol of iron (III) chloride hexahydrate (a molar ratio of 1:2:4 iron (III) chloride:fumaric acid:sodium hydroxide). The first solution was added to the second, resulting in immediate precipitate formation. The resulting mixture was stirred for 30 hours using a magnetic stirrer. The product was obtained by vacuum filtration and washed with copious amounts of de-ionized water. It was then allowed to dry under vacuum, yielding 3.156 g (9.93 mmol, 66.5%) of amorphous iron basic carboxylate powder. Within the present disclosure, the term amorphous refers to a substance that does not have any appreciable repeating crystalline structure. Thermogravimetric analysis was carried out on Product 1, which indicated a molecular formula of $Fe_2(C_4H_2O_4)_4(OH_2)_2$, and a formula weight of 638 g/mol.

Figure 3:
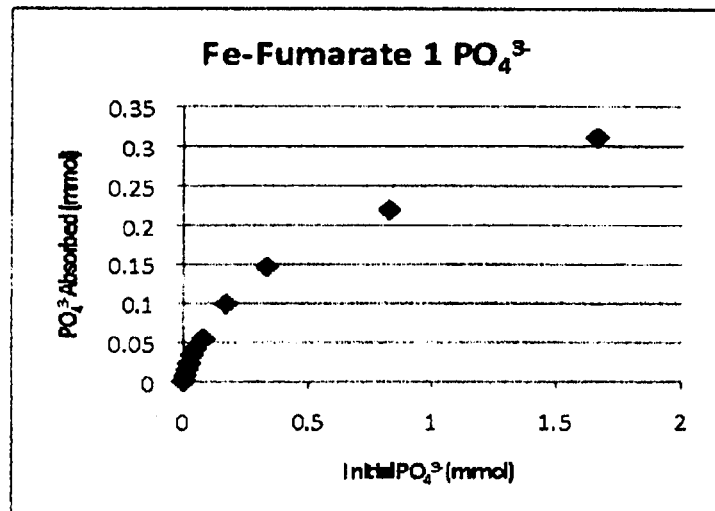
FIG. 3 is a Langmuir isotherm for adsorption of phosphate by iron (III) fumarate Product 1 of the present disclosure.

Phosphate adsorption experiments were performed for Product 1. Phosphate solutions of increasing concentrations were prepared and added to 0.05 grams of iron fumarate prepared as stated. The volume of phosphate solution added was kept constant at 15 mL. After two days, the phosphate concentration was measured using a colorimeter. A Langmuir isotherm curve was then prepared from this data as shown in FIG. 3.

EXAMPLE 2

In another example, iron fumarate (Product 2) was prepared by adding 300 mL de-ionized water to 30.03 mmol of fumaric acid and 90.46 mmol of sodium hydroxide. Another aqueous solution was prepared by adding 300 mL de-ionized water to 30.03 mmol of iron (III) chloride hexahydrate (a molar ratio of 1:1:3 iron (III) chloride:fumaric acid:sodium hydroxide). The first solution was added to the second, resulting in immediate precipitate formation. The resulting mixture was stirred for about 7 days using a magnetic stirrer. The product was obtained by vacuum filtration and washed with de-ionized water. It was then allowed to dry under vacuum, yielding 5.776 g of product.

Figure 4:
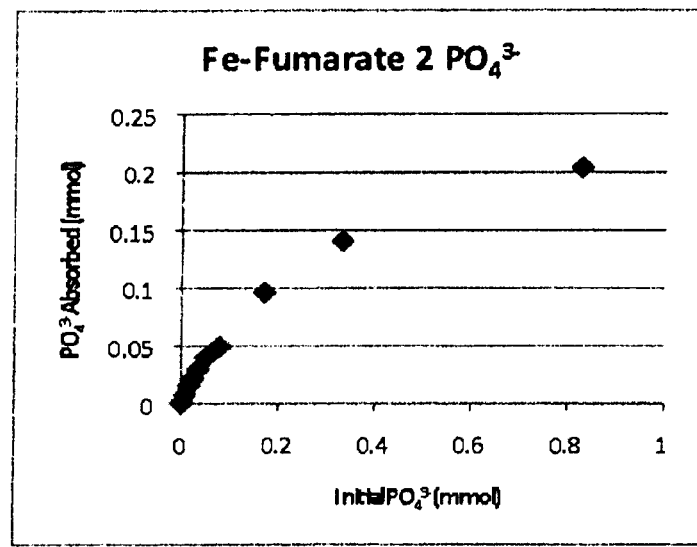
FIG. 4 is a Langmuir isotherm for adsorption of phosphate by iron (III) fumarate Product 2 of the present disclosure.

Phosphate adsorption experiments were again performed for Product 2. Phosphate solutions of increasing concentrations were prepared and added to 0.05 grams of iron fumarate prepared as stated. The volume of phosphate solution added was kept constant at 15 mL. After two days, the phosphate concentration was measured using a colorimeter. A Langmuir isotherm curves was then prepared from this data as shown in FIG. 4.

EXAMPLE 3

In another example, iron fumarate (Product 3) was prepared by adding 0.09 mmol (3.6 g) sodium hydroxide to 300 mL de-ionized water in a 500 mL Erlenmeyer flask. To this solution was added 0.03 mmol (3.482 g) fumaric acid, which was stirred to dissolution. In a 1 L Erlenmeyer flask 0.03 mmol (8.109 g) of iron chloride hexahydrate was stirred to dissolution in 300 ml of de-ionized water. While stirring slowly, the sodium hydroxide/fumaric acid solution was added to the iron chloride solution. The resulting precipitate was collected by vacuum filtration with a fine porosity glass frit. The collected precipitate was washed with de-ionized water until no chloride was detected (via formation of silver chloride). The precipitate was then dried at room temperature under vacuum producing the final product.

Figure 5:
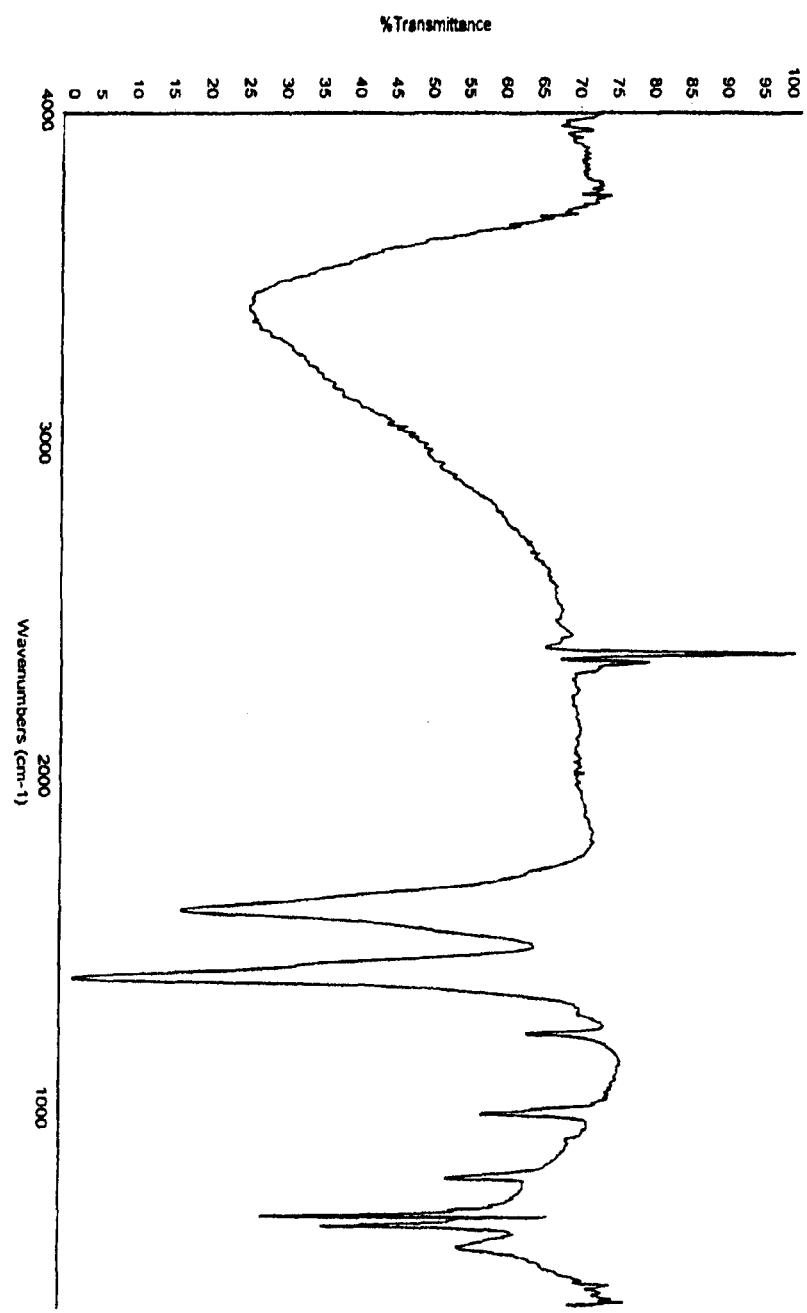
FIG. 5 is a graph of the infrared spectrum of iron fumarate.
Figure 6:
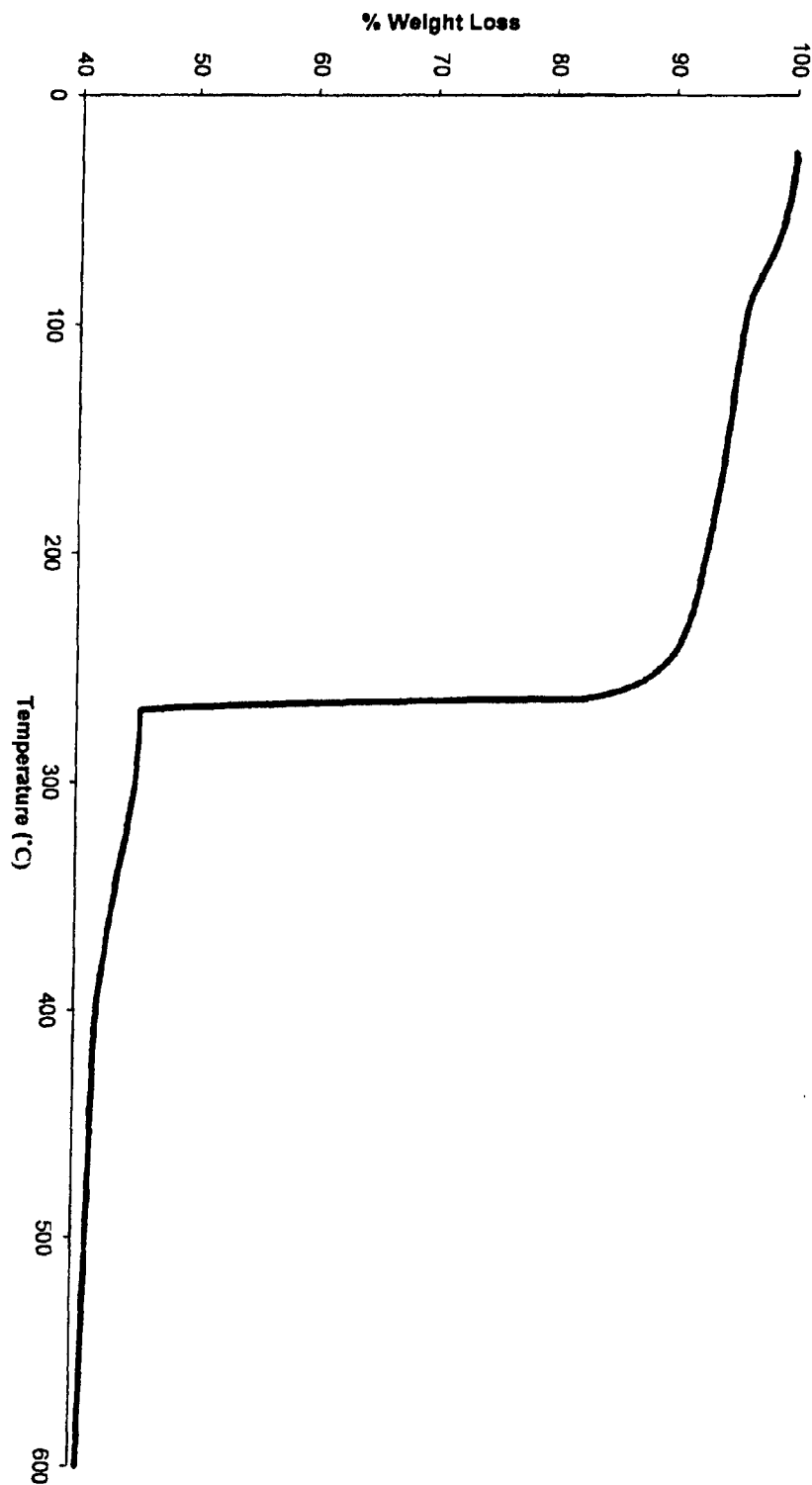
FIG. 6 is a graph of a thermogravimetric analysis of iron fumarate.

The surface area of the iron fumarate of Product 3 was measured using a Quantachrome Nova 1200 by the 6 point BET method. The specific surface area was determined to be 18.80 $m^2$/g. The dry density of Product 3 was measured using a graduated cylinder and balance and found to be 0.44 g/$cm^3$. FIG. 5 illustrates the infrared spectrum of Product 3, while FIG. 6 illustrates the results of a thermogravimetric analysis of the same. The formula of the resultant product is indicated by thermogravimetric analysis as approximately $Fe(C_4H_2O_4)(OH).0.5H_2O$.

Figure 7:
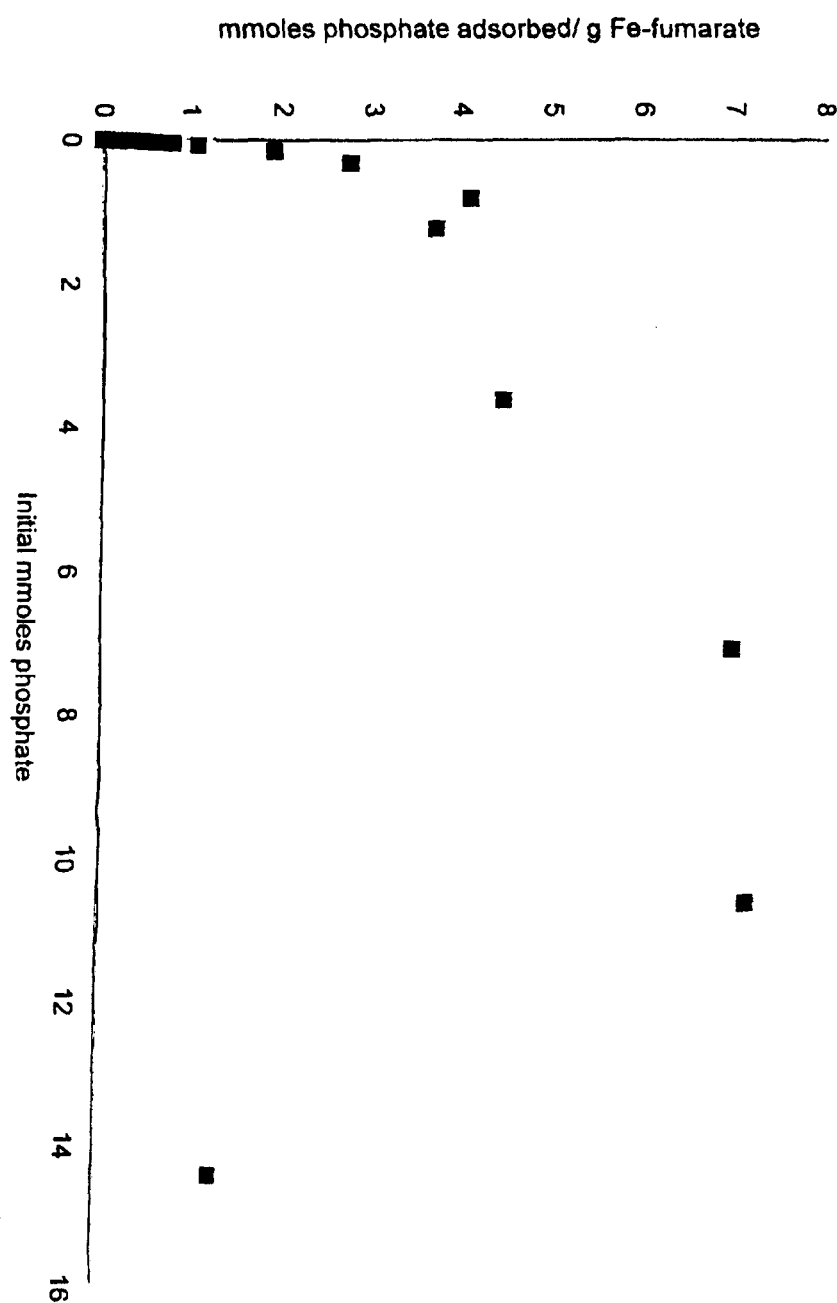
FIG. 7 is a graph corresponding to phosphate update absorption ability of iron fumarate of the present disclosure.
Figure 8:
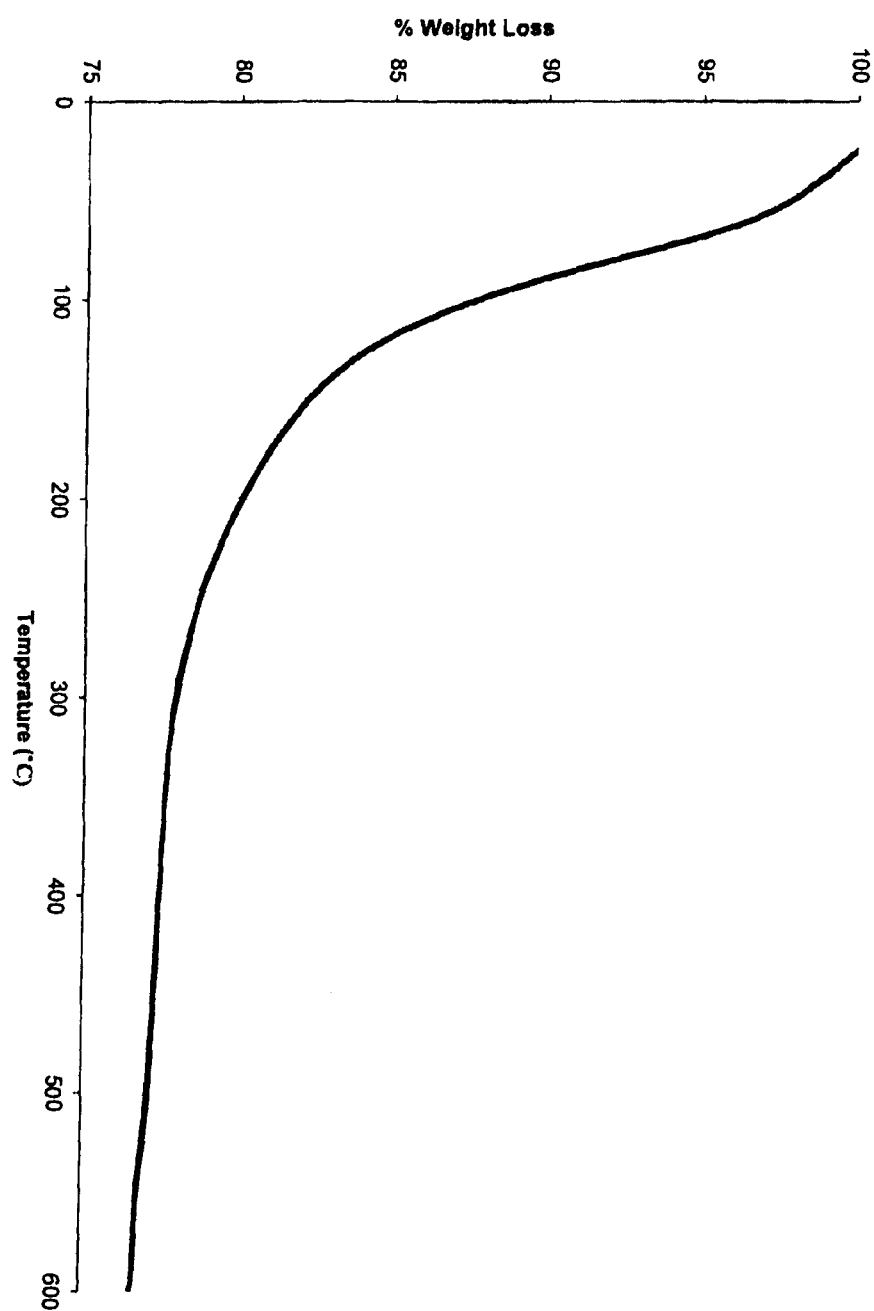
FIG. 8 is a graph of a thermogravimetric analysis of an adsorption product of iron fumarate and adsorbed phosphate.
Figure 9:
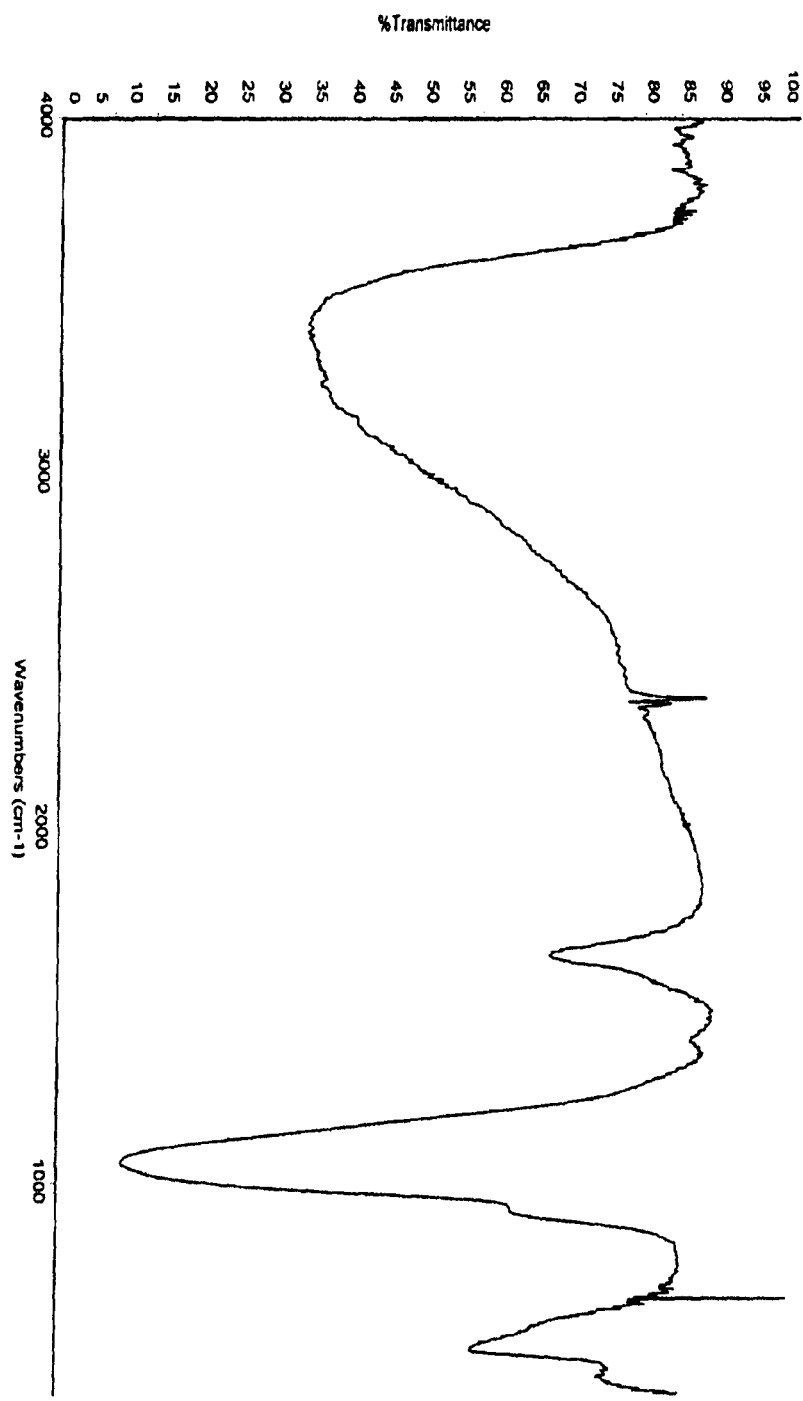
FIG. 9 is a graph of the infrared spectrum of the adsorption product.

For testing of Product 3, stock solutions of phosphate were prepared using sodium phosphate monobasic hydrate. 15 mL of each solution was added to a 20 mL scintillation vial and 50 mg of iron fumarate (Product 3) was added to each vial. The vials were shaken to ensure uniform distribution of iron fumarate and allowed to react while mixing for a period of two days. After 48 hours, samples were filtered using 10 mL disposable syringes and 0.45 micron syringe filters. The solutions were diluted with deionized water until phosphate concentrations were within 0.05 to 2.5 mg/L, as measured using a Hach colorimeter. FIG. 7 illustrates the phosphate update adsorbed with as a result of this experiment. FIG. 8 illustrates the results of a thermogravimetric analysis of the resultant product, while FIG. 9 illustrates the infrared spectrum.

Infrared spectroscopy suggests that fumaric acid has been replaced by phosphate in the test reactions described above. Hence the reaction may be more characteristic of a chemical reaction than adsorption per se.

Figure 10:
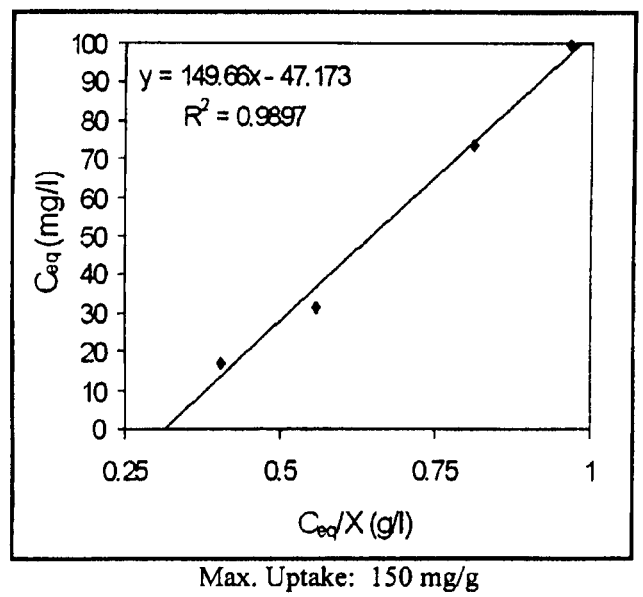
FIG. 10 is a Langmuir isotherm for adsorption of arsenate by iron (III) fumarate.
Figure 11:
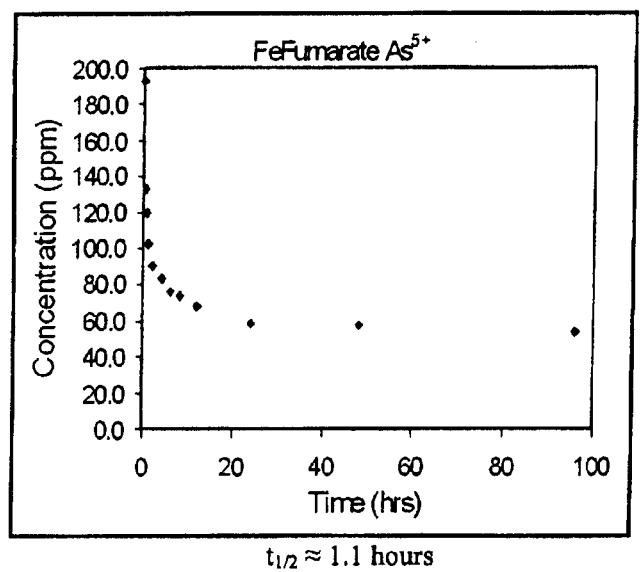
FIG. 11 is a graph of sorption kinetics for iron (III) fumarate adsorption of arsenate.

From the foregoing, it was determined that the capacity for adsorption of phosphate of the various iron fumarate products exceeded 480 mg/g. The iron fumarate products of the present disclosure were also tested for absorbency of arsenate and found to have the capacity adsorb 150 mg/g of adsorbent (15% by weight). FIG. 10 illustrates a Langmuir isotherm of iron (III) fumarate absorbency of arsenate ($As^{5+}$). FIG. 11 illustrates the kinetics of the adsorption.

EXAMPLE 4

In another example of the effectiveness of the iron coordination polymer of the present disclosure, ground water contaminated with arsenic was collected from a well in central Oklahoma. The sample was analyzed by graphite furnace atomic absorption spectroscopy and found to contain 54 ppm of arsenic. 4.9 g of this ground water was treated 58 mg of the iron fumarate coordination polymer of the present disclosure for 12 hours. Analysis of the treated sample showed an arsenic concentration of 0.24 ppb, a 99.6% reduction.

EXAMPLE 5

In another test of efficacy, water was collected from an outdoor fountain on the campus of Oklahoma Christian University. The water was analyzed and found to contain 13 ppb of arsenic. Treatment of 10.1 g of this water with 10.7 mg of the iron fumarate coordination polymer of the present disclosure for 12 hours reduced the arsenic concentration to 0.16 ppb.

EXAMPLE 6

Water was prepared that simulated the composition of oil sands tailings pond water. The composition of the water is given in Table 1. Treatment of 10.0 g of this solution with 9.8 mg of the iron fumarate coordination polymer of the present disclosure for 12 hours reduced the arsenic concentration to 0.66 ppm.

TABLE 1

| Oil Sands pond water composition | |
|---|---|
| Element | Concentration |
| Sodium | 540 ppm |
| Calcium | 25 ppm |
| Magnesium | 12 ppm |
| Chloride | 90 ppm |
| Bicarbonate | 950 ppm |
| Sulfate | 290 ppm |
| Ammonia | 14 ppm |

TABLE 1-continued

Oil Sands pond water composition

| Element | Concentration |
|---------|---------------|
| Copper  | 660 ppb       |
| Arsenic | 15 ppb        |
| Lead    | 190 ppb       |

EXAMPLE 7

In another example, water was prepared that contained 1000 ppm of arsenic (as potassium hydrogen arsenate) as a simulant for waste water from polishing of gallium arsenide wafers. Treatment of 10.0 g of this solution with 2.0 g of the iron fumarate coordination polymer of the present disclosure reduced the arsenic concentration to 5.5 ppb, a 99.99% reduction.

The above examples are only exemplary methods in which the iron fumarate products of the present disclosure may be formed. It is understood that one of skill in the art will readily adapt these methods to large scale production of the iron fumarate products if so desired.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

REFERENCES

[1] Masscheyleyn, P. H.; Delaune, R. D.; Patrick, W. H. Jr. *J. Environ Qual.* 1991, 20, 522-527.
[2] Masscheyleyn, P. H.; Delaune, R. D.; Patrick, W. H. Jr. *Environ Sci. Technol.* 1991, 25, 1414-1419.
[3] Korte, N. E.; Fernando, Q. *Crit. Rev. Environ. Control* 1991, 21, 1-39.
[4] Goldber, S. *Soil Sci. Am. J.* 2002, 66, 413-421.
[5] Khaodhiar, S.; Azizian, M. F.; Osathaphan, K.; Nelson, P. O. *Water, Air, and Soil Pollution,* 2000, 119, 105.
[6] Hsia, T. H.; Lo, S. L.; Lin, C. F. *Chemosphere,* 1992, 25, 1825-1837.
[7] Hingston, J. F.; Posner, A. M.; Quirk, J. P. *Discuss. Faraday Soc.* 1971, 52, 334-342.
[8] Ferguson, J. F.; Anderson, M. A. "Chemical forms of arsenic in water supplies and their removal. In Chemistry of water supply treatment and distribution"; Rubin, A. J., Ed.; *Ann Arbor Science,* Ann Arbor, Mich., 1974; pp. 137-158.
[9] Pierce, M. L.; Moore, C. B. *Water Res.,* 1982, 16, 1247-1253.
[10] Pierce, M. L.; Moore, C. B. *Environ. Sci. Technol.,* 1980, 14, 214-216.
[11] Singh, D. B.; Prasad, G.; Rupainwar, D. C.; Singh, V. N. *Water Air Soil Pollut.* 1988, 42, 373-386.
[12] Raven, K. P., Jain, A.; Loeppert, R. H. *Environ Sci. Technol.* 1998, 32, 344-349.

What is claimed is:

1. A method comprising:
   combining an alkaline aqueous solution of sodium fumarate with an aqueous solution of iron chloride to form a mixture, whereby an amorphous iron coordination polymer is formed as a precipitate in the mixture.

2. The method of claim 1, further comprising vacuum filtering the amorphous iron coordination polymer from the mixture.

3. The method of claim 1, further comprising washing the amorphous iron coordination polymer with de-ionized water.

4. The method of claim 1, further comprising vacuum drying the amorphous iron coordination polymer.

5. The method of claim 1, further comprising exposing the amorphous iron coordination polymer to contaminated water to bind contaminants.

6. The method of claim 5, wherein the contaminant is a form of arsenic.

7. The method of claim 5, wherein the contaminant is a form of phosphorus.

8. A method comprising:
   mixing an alkaline aqueous solution of sodium fumarate with an aqueous solution of iron chloride to form a mixture, whereby an amorphous iron coordination polymer formed as a precipitate in the mixture; and
   exposing contaminated water to the amorphous iron coordination polymer.

9. The method of claim 8, wherein the amorphous iron coordination polymer has the approximate formula of $Fe(O_2CCH=CHCO_2)OH*1.5H_2O$.

10. The method of claim 8, wherein the contaminant is a form of arsenic.

11. The method of claim 8, wherein the contaminant is a form of phosphorus.

12. A method comprising:
    precipitating iron (III) fumarate as an amorphous iron coordination polymer by mixing an alkaline aqueous solution of sodium fumarate with an aqueous solution of iron chloride;
    vacuum filtering the precipitate from the mixture of sodium fumarate and aqueous iron chloride;
    rinsing the precipitate with de-ionized water; and
    vacuum drying the precipitate.

13. The method of claim 12, wherein said mixing is accomplished by stirring the mixture of sodium fumarate and aqueous iron chloride for at least 24 hours before vacuum filtering.

14. The method of claim 12, further comprising exposing the dried precipitate to a body of water to bind arsenate.

15. The method of claim 12 further comprising exposing the dried precipitate to a body of water to bind phosphate.

* * * * *